ary Examiner*—Curtis R. Davis
United States Patent [19]

Vora

[11] 4,376,225
[45] Mar. 8, 1983

[54] DEHYDROGENATION PROCESS UTILIZING INDIRECT HEAT EXCHANGE AND DIRECT COMBUSTION HEATING

[75] Inventor: Bipin V. Vora, Elk Grove Village, Ill.

[73] Assignee: UOP Inc., Des Plaines, Ill.

[21] Appl. No.: 290,119

[22] Filed: Aug. 5, 1981

[51] Int. Cl.³ .......................................... C07C 5/333
[52] U.S. Cl. .................................. 585/659; 585/658; 585/660
[58] Field of Search ........................ 585/658, 659, 660

[56] References Cited

U.S. PATENT DOCUMENTS

| | | | |
|---|---|---|---|
| 2,959,626 | 11/1960 | Krausse et al. | 585/430 |
| 3,375,288 | 3/1968 | de Rosset | 585/403 |
| 3,391,218 | 7/1968 | Bloch | 585/660 |
| 3,437,703 | 4/1969 | Reitmeier et al. | 585/443 |
| 3,448,165 | 6/1969 | Bloch | 585/660 |
| 3,502,737 | 3/1970 | Ghublikian | 585/441 |
| 3,515,766 | 6/1970 | Root et al. | 585/402 |
| 3,647,911 | 3/1972 | Vesely et al. | 585/660 |
| 3,649,566 | 3/1972 | Hayes et al. | 252/470 |
| 3,714,281 | 1/1973 | Hayes et al. | 585/433 |
| 3,745,112 | 7/1973 | Rausch | 208/139 |
| 3,761,390 | 9/1973 | Greenwood et al. | 208/65 |
| 3,855,330 | 12/1974 | Mendelsohn et al. | 585/441 |
| 3,904,703 | 9/1975 | Lo et al. | 585/659 |
| 3,907,511 | 9/1975 | Forbes et al. | 422/191 |
| 3,978,150 | 8/1976 | McWilliams, Jr. | 585/659 |

*Primary Examiner*—Curtis R. Davis
*Attorney, Agent, or Firm*—James R. Hoatson, Jr.; John F. Spears, Jr.; William H. Page II

[57] ABSTRACT

A multiple reaction zone process for dehydrogenating light hydrocarbons, preferably propane, is disclosed. The feed stream and intermediate streams are first heated by indirect heat exchange to temperatures slightly below the desired inlet temperature of the dehydrogenation catalyst beds. These streams are then transported to a location which is in close proximity of the dehydrogenation catalyst bed and further heated by the selective combustion of hydrogen present in these streams through the use of beds of oxidation catalyst. This eliminates lengthy high temperature reactant residence times in transfer lines extending between fired heaters and the dehydrogenation catalyst beds, thereby reducing thermal cracking of the feed and increasing the selectivity of the process. The process has special utility with stacked moving bed reactors, which have larger volume reactant transfer lines.

20 Claims, 1 Drawing Figure

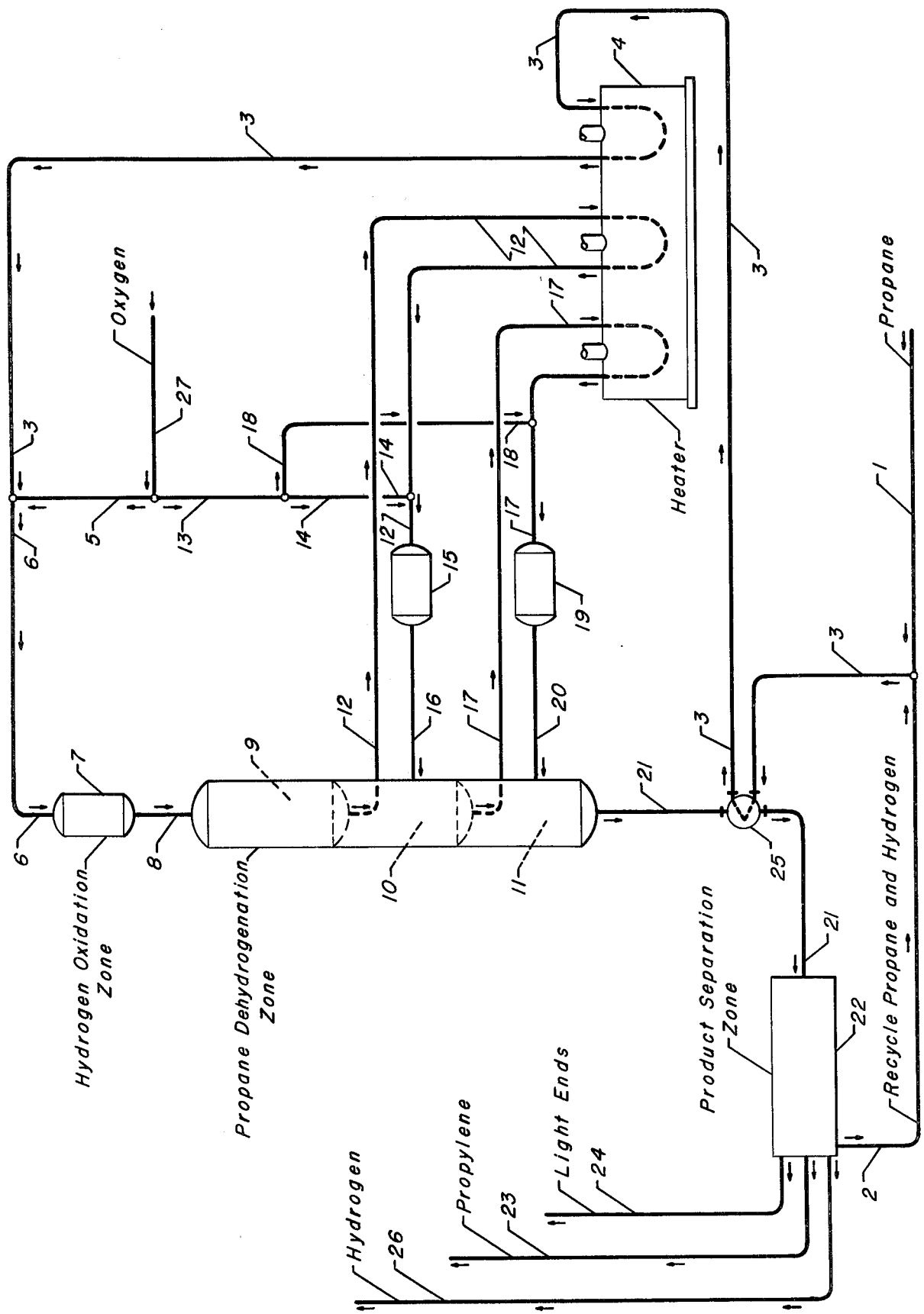

DEHYDROGENATION PROCESS UTILIZING INDIRECT HEAT EXCHANGE AND DIRECT COMBUSTION HEATING

FIELD OF THE INVENTION

The invention relates to the processing of mineral oils and more specifically to a process for the dehydrogenation of hydrocarbons. The invention is directly concerned with the production of light olefinic hydrocarbons by the dehydrogenation of light paraffins such as propane, with the overall dehydrogenation being performed in a number of sequential reaction stages. The field of the subject invention may be further narrowed to those dehydrogenation processes which utilize elemental oxygen to selectively consume hydrogen released during the dehydrogenation reaction.

PRIOR ART

The dehydrogenation of light hydrocarbons is a highly developed process. For instance, processes for the dehydrogenation of paraffins are described in U.S. Pat. Nos. 3,391,218; 3,448,165; 3,649,566; 3,647,911; and 3,714,281. These references describe various catalysts and process conditions which may be employed. The preferred dehydrogenation catalyst is described in U.S. Pat. No. 3,745,112.

A typical prior art process flow comprises the admixture of the feed hydrocarbon with hydrogen and the heating of the feed stream through indirect heat exchange with the dehydrogenation zone effluent stream. The feed stream may comprise recycled unconverted hydrocarbons and will normally comprise recycled hydrogen. After being heated in the feed-effluent heat exchanger, the feed stream is further heated by passage through a heater which is typically a fired heater or furnace. The feed stream is then contacted with a bed of dehydrogenation catalyst, which may be either a fixed or fluidized bed of catalyst. The dehydrogenation reaction is very endothermic and the entering reactants are quickly cooled to temperatures at which the dehydrogenation reaction does not proceed at an acceptable rate. To counteract this cooling effect of the reaction, heat may be supplied to the bed of dehydrogenation catalyst by indirect heat exchange with circulating high temperature fluids or by a rapid turnover of catalyst in a fluidized bed system.

Another method of supplying the necessary heat of reaction is to remove the reactants from the bed of dehydrogenation catalyst and to heat the reactants externally through the use of a heater. In this instance, the reactants which emerge from the first bed of dehydrogenation catalyst are passed through a heater which may be similar to the initial feed heater. The thus-heated reactants are then passed through a second bed of dehydrogenation catalyst. This contacting-reheating sequence may be repeated as many times as is desired. A process for the dehydrogenation of ethylbenzene utilizing interstage reheating of the reactants is described in U.S. Pat. No. 2,959,626.

Still another method of reheating the reactants in a multistage dehydrogenation process is through the use of superheated steam, which can be admixed into the feed stream to the first reaction stage and/or to each subsequent reaction stage. This type of interstage reheating is normally associated with the dehydrogenation of alkylaromatic hydrocarbons and is described in U.S. Pat. No. 3,515,766.

Another system utilized for the dehydrogenation of light paraffins employs a large number of separate reaction zones. Each of the reaction zones is used for a short time period for the dehydrogenation of the entering feed hydrocarbon, with the dehydrogenation producing a sizable amount of carbonaceous deposits upon the catalyst. The flow of the feed stream is then diverted to a different reaction zone, and the catalyst present in the previously used reaction zone is regenerated by contact with an oxygen-containing gas stream. The combustion of the carbonaceous deposits located on the dehydrogenation catalyst regenerates and reheats the catalyst and may produce excess heat which may be stored for use in a subsequent dehydrogenation reaction. The thus-regenerated and heated bed of dehydrogenation catalyst is then once again used for dehydrogenation, and the regeneration procedure is applied to catalyst beds which were used in the interim.

Whatever form the reaction zone takes, it is customary for the effluent stream of the dehydrogenation reaction zone to be passed through the feed-effluent heat exchanger for heat recovery and to then be cooled sufficiently to cause a partial condensation of the effluent stream. The partial condensation facilitates the easy separation of the bulk of the hydrogen from the other components of the effluent stream, with a portion of the hydrogen being removed as a net product gas and a second portion normally being recycled to the dehydrogenation reaction zone. The remaining mixture of saturated and unsaturated hyrocarbons and by-products is passed into the appropriate products recovery facilities, which will typically comprise a first stripping column which removes light ends having boiling points below that of the desired product and a second fractionation column which separates the remaining hydrocarbons into product and recycle streams.

It is also known in the prior art to pass oxygen into a dehydrogenation zone for the purpose of reacting the oxygen with hydrogen released during the dehydrogenation reaction to thereby liberate heat and to consume hydrogen. The processes known to employ this technique utilize a hydrogen oxidation catalyst in an attempt to selectively oxidize the hydrogen rather than feed or product hydrocarbons also present in the dehydrogenation zone. For instance, U.S. Pat. No. 3,437,703 issued to R. E. Reitmeier et al discloses a dehydrogenation process which may utilize either a "homogeneous catalyst system" in which oxidation and dehydrogenation catalysts are admixed or a layered system of individual catalyst beds referred to as a "multi bed" system. This reference indicates that the process may be utilized in the dehydrogenation of butane. It appears that in this reference the feed stream to the dehydrogenation zone always comprises an admixture of the feed hydrocarbon and steam or an admixture of the feed hydrocarbon, steam and oxygen, with apparently no disclosure of the recycling of hydrogen to the dehydrogenation zone.

Two other references also disclose the utilization of oxygen within a dehydrogenation zone. U.S. Pat. No. 3,502,737 issued to J. R. Ghublikian presents a process for the dehydrogenation of ethylbenzene which indicates catalyst activity and stability are maintained by the careful control of the amount of oxygen which is present and by a reduction in the steam which is used in the reaction zone. An oxygen-containing gas such as air is supplied both initially and at interstage points in a carefully controlled manner. It is believed that the teaching of this reference is limited to the use of a catalyst system comprising a physical admixture of the hydrogen oxidation catalyst and the dehydrogenation catalyst, with the presence of oxygen being credited with assisting in the prevention of carbon deposits on the surface of catalytically active sites of the dehydrogenation catalyst. U.S. Pat. No. 3,855,330 issued to J. C. Mendelsohn et al also discloses a dehydrogenation process using sequential beds of dehydrogenation catalyst and oxidation catalyst. According to the teachings of this reference, it is preferred that oxygen is introduced only after substantial conversion of the feed hydrocarbon. It is taught in this reference that it is desirable that oxygen does not come into contact with the dehydrogenation catalysts, and that the major part or all of the added oxygen is consumed within the bed of oxidation catalyst.

The use of multistage reaction systems in which the catalyst moves downward by gravity flow between different reaction stages is disclosed in U.S. Pat. Nos. 3,761,390 and 3,907,511. These systems are basically directed to the reforming of petroleum naphthas, but could be adapted to the processing of other hydrocarbons. The first of these two references is also pertinent for its showing of the use of interstage heaters in a multistage endothermic process. In its preferred embodiment, the subject inventive concept is directed to a dehydrogenation process employing a similar stacked multistage reactor having catalyst flow by gravity between sequential stages and utilizing interstage heating of reactant streams passing between different stages. A process employing this type of reaction zone for the dehydrogenation of paraffins is disclosed in U.S. Pat. No. 3,978,150.

BRIEF SUMMARY OF THE INVENTION

The invention provides a dehydrogenation process for light hydrocarbons wherein the amount of thermal cracking of the feed hydrocarbon to undesired by-products is reduced. The invention is directed to a multistage dehydrogenation process in which, due to the dehydrogenation zone configuration, it is necessary to transport the reactants a considerable distance between interstage heaters and the next bed of dehydrogenation catalyst. The inventive concept comprises heating the reactants in the interstage heaters only to the threshold level at which thermal cracking occurs to a significant extent, transporting the thus-heated reactants to a location in close proximity to the downstream bed of dehydrogenation catalyst, and then heating the reactants to the desired inlet temperature of the dehydrogenation stage by contacting the process stream with a bed of oxidation catalyst under conditions such that hydrogen present in the process stream is to a large extent selectively combusted.

A broad embodiment of the subject invention may be characterized as a process for the dehydrogenation of hydrocarbons which comprises the steps of admixing oxygen into a heated feed stream comprising a $C_2-C_8$ hydrocarbon and hydrogen; contacting the feed stream with a first bed of oxidation catalyst which preferentially oxidizes hydrogen as compared to the $C_2-C_8$ hydrocarbon; contacting the effluent of the first bed of oxidation catalyst with a first bed of dehydrogenation catalyst located within a dehydrogenation zone; heating the effluent of the first bed of dehydrogenation catalyst by indirect heat exchange; admixing oxygen into the heated effluent of the first bed of dehydrogenation catalyst; contacting the effluent of the first bed of dehydrogenation catalyst with a second bed of oxidation catalyst; contacting the effluent of the second bed of oxidation catalyst with a second bed of dehydrogenation catalyst located within the dehydrogenation zone; and recovering from a dehydrogenation zone effluent stream an unsaturated $C_2-C_8$ product hydrocarbon corresponding to the feed hydrocarbon and hydrogen and recycling a portion of the hydrogen to the dehydrogenation zone as part of the feed stream.

BRIEF DESCRIPTION OF THE DRAWING

The Drawing illustrates a preferred embodiment of the invention as it may be employed for the dehydrogenation of propane. A feed stream is formed by the admixture of a charge stream of propane from line 1 with recycle propane and hydrogen from line 2. The feed stream is heated in the feed effluent heat exchanger 25 and a fired heater 4 before admixture with oxygen from line 5. The resulting admixture is passed through line 6 into a hydrogen oxidation zone 7 located in close proximity to a propane dehydrogenation zone. The feed stream is then further heated to the desired inlet temperature of the first dehydrogenation stage 9 by the combustion of hydrogen in the hydrogen oxidation zone 7. This eliminates the need to fully heat the feed stream to the desired inlet temperature in the heater 4 and to then transfer the heated feed stream through a considerable length of large diameter conduit at a high temperature, which promotes the thermal cracking of the propane to undesired by-products. Instead, the feed stream is maintained at the higher temperatures for only the shorter time period required to travel between the hydrogen oxidation zone 7 and the first propane dehydrogenation stage 9.

The effluent of the first propane dehydrogenation stage is passed through the heater 4 in line 12 and is thereby brought near to but not into the temperature range at which significant thermal cracking occurs and is then admixed with additional oxygen. This stream is then passed through a second hydrogen oxidation zone 15 and into a second propane dehydrogenation stage 10. In a similar manner, the effluent of the second dehydrogenation stage is carried through the heater in line 17, admixed with oxygen and passed through a third hydrogen oxidation zone 19 before entering the third dehydrogenation stage 11. The effluent of the propane dehydrogenation zone is removed in line 21 and passed into a product separation zone 22 which produces product streams of propylene and hydrogen and the recycle stream of line 2.

DETAILED DESCRIPTION

The dehydrogenation of light hydrocarbons to produce the corresponding unsaturated hydrocarbons is practiced commercially to provide feedstocks for the petroleum and petrochemical industries. It is expected that there will be increased utilization of these processes in the near future to supply the olefins required for the production of increased amounts of lead-free high octane motor fuels, motor fuel blending components, and as feedstocks for various petrochemical operations.

In any hydrocarbon conversion process, it is normally desirable to produce a minimum amount of by-products. This is also true in the case of light hydrocarbon dehydrogenation. A large amount of effort is therefore directed into the development of catalysts which are highly selective for dehydrogenation. Despite any high level of selectivity which is obtained by the catalyst, there are other chemical reactions which may occur and which may detract from the selectivity of the process. Probably the most significant of these undesired chemical reactions is the thermal cracking of the feed hydrocarbons. For instance, at a temperature above 600° C. and particularly at 660° C., the thermal cracking of propane becomes significant. The amount of thermal cracking which occurs is directly proportional to the temperature and to the residence time that the propane is maintained at the elevated temperature. The thermal cracking of propane lowers the yield of propylene and is therefore an undesirable side reaction. However, in the catalytic dehydrogenation of propane it is normally desired to have the inlet temperature, which is the temperature of the propane-containing stream as it enters the catalyst bed, in the range of about 650–700° C. Since these two temperature ranges overlap, the amount of thermal cracking which occurs can reach a level at which it has a definite detrimental economic effect on the overall process if the feed propane is maintained at the desired inlet temperatures for any significant time.

It is normally desired to operate a dehydrogenation process at a minimum practical pressure. This desire influences the design of the reactor, the transfer lines used within the process and the other equipment such as heaters and heat exchangers. In particular, in order to obtain a low pressure drop through components such as heaters and heat exchangers, the linear velocity of the reactants is normally reduced through the use of conduits having a large volume or through the use of a larger number of conduits. This results in a high residence time for the reactants within the heater. Furthermore, the reactants must often be transported a considerable distance from the heater to the inlet of the dehydrogenation zone. When they must be also reheated and returned to the dehydrogenation points at intermediate points, the total residence time in the heaters and in the interconnecting transfer lines between the heater and the dehydrogenation zone can become quite long. A considerable amount of thermal cracking can occur in these lengthy residence times. This problem is compounded because the temperature drop which occurs in most process lines normally makes it necessary for the actual heater outlet temperature to exceed the desired reactor inlet temperature. This higher temperature further increases the potential for thermal cracking. The problems associated with the thermal cracking of light hydrocarbons during a dehydrogenation process are therefore accentuated when the preferred multistage gravity flow reaction system employing interstage reheating through the use of a fired heater is employed as the dehydrogenation zone.

It is an objective of the subject invention to provide a process for the dehydrogenation of light hydrocarbons. It is a specific objective of the subject invention to provide a process for the dehydrogenation of $C_2$–$C_8$ hydrocarbons. A particular objective of the subject invention is to reduce thermal cracking which occurs in a process for the dehydrogenation of propane. A further objective of the subject invention is to reduce thermal cracking in a dehydrogenation process which employs a stacked multistage reaction zone having interstage reactant heating and gravity flow of catalyst between reaction stages.

In the subject invention, the total amount of thermal cracking which occurs in a dehydrogenation process is reduced by minimizing the time during which the feed hydrocarbon is maintained at an elevated temperature at which thermal cracking readily occurs. For instance, in the dehydrogenation of propane, the heater outlet temperature is limited to approximately 650°–660° C. and the propane is kept below this temperature until entering the oxidation catalyst. That is, the heater outlet temperature is limited to the lower temperatures at which the thermal cracking of the propane is rather limited. The heated feed stream is then transported to the bed of dehydrogenation catalyst, and only at this point is it heated to the desired inlet temperature of the dehydrogenation catalyst bed. This final and rather small amount of heating is the result of direct combustion heating of the reactants by the highly exothermic reaction of oxygen and the hydrogen over a selective oxidation catalyst. The heat provided by this combustion should be sufficient to raise the temperature of the entering reactants between about 10–20 Centigrade degrees. The selective hydrogen oxidation catalyst utilized in this reaction is contained in either a very small reactor mounted near the inlet of each dehydrogenation stage or in a separate bed of catalyst located within and perhaps immediately next to the bed of dehydrogenation catalyst. For instance, the oxidation catalyst may be disposed in a relatively thin annular bed located within the centerpipe region of a larger annular bed of dehydrogenation catalyst. The use of small reactors located on the outside of the vessel containing the dehydrogenation catalyst is preferred.

A more complete understanding of the inventive concept may be obtained by a review of the Drawing, which is a simplified diagram of a propane dehydrogenation process operated according to the preferred embodiment of the invention. This presentation of one embodiment of the invention is not intended to exclude from the scope of the inventive concept those other embodiments set out herein or other reasonable and normal modifications of the inventive concept. Referring now to the Drawing, a charge stream of propane from line 1 is combined with a recycle stream comprising propane and hydrogen from line 2 to form a feed stream carried by line 3. This feed stream is heated by indirect heat exchange in the feed-effluent heat exchange means 25 and is then passed into a fired heater 4. This heater is operated in a manner which increases the temperature of the feed stream to approximately 650° C., which is lower than the desired dehydrogenation inlet temperature.

The feed stream is removed from the heater at this approximate temperature range and combined with a stream of oxygen from line 5. The heated feed stream which now contains a small amount of oxygen continues through line 6 and is passed into a first bed of oxidation catalyst located within a hydrogen oxidation zone 7. The contacting of the entering feed stream with the oxidation catalyst at the elevated temperatures results in a combustion reaction between the hydrogen and oxygen present in the feed stream to the extent that these two reactants are available. The first hydrogen oxidation zone is located within close proximity of the main process vessel of the propane dehydrogenation zone to reduce the time at which the propane is at the elevated temperature. The effluent stream of the first oxidation zone is passed through line 8 and contacted with a bed of dehydrogenation catalyst in a first dehydrogenation stage 9. This results in the dehydrogenation of a portion of the propane present in the entering process stream and a cooling of the reactants due to the endothermic nature of the dehydrogenation reaction. The effluent stream of the first bed of dehydrogenation catalyst is collected and removed from the first dehydrogenation stage through line 12 and passed through one or more heating coils in the fired heater 4. The materials passing through line 12 are heated within the heater to a temperature near the desired inlet temperature of the second dehydrogenation stage but not to a temperature which would result in significant thermal cracking of the remaining propane. It is preferred that this stream has a temperature below 650° C. prior to entering the downstream bed of oxidation catalyst.

The thus-heated effluent of the first dehydrogenation stage is carried to a point close to the second bed of dehydrogenation catalyst, admixed with a small stream of oxygen derived from line 27 via lines 13 and 14 and is then passed into a second hydrogen oxidation zone 15. Within this zone, the effluent stream of the first dehydrogenation stage is contacted with a second bed of oxidation catalyst and thereby heated through the combustion of hydrogen. The effluent of the second oxidation zone preferably has a temperature above 655° and more preferably above 670° C. This stream is passed into a second dehydrogenation stage 10 through line 16. A further portion of the propane which enters the dehydrogenation zone is converted to propylene within the second dehydrogenation stage to form an effluent stream removed in line 17 and passed through the heater 4. A third small stream of oxygen carried by line 18 is admixed into the effluent of the second dehydrogenation stage and the resultant heated mixture is passed into a third oxidation zone 19 and heated by contact with the selective hydrogen oxidation catalyst. The effluent of the third oxidation zone is passed into the third dehydrogenation stage 11 through line 20. The effluent stream of the propane dehydrogenation zone is removed in line 21 and cooled by indirect heat exchange in means 25. It is then passed into a product separation zone 22 wherein the product propylene is recovered through the use of one of the several known product separation and purification methods. The product propylene is removed through line 23 in a stream of light ends such as methane and ethane produced as by-products of the dehydrogenation reaction are removed in line 24. Excess hydrogen produced in the dehydrogenation reaction is removed in line 26, with unconverted propane and some recycled hydrogen being returned to the dehydrogenation zone through line 2.

The subject invention has the advantage of reducing thermal craking, especially in process operated at low pressures which result in long residence times in transfer conduits and heaters. It therefore helps to resolve the conflict which occurs between the desire to operate the dehydrogenation process at a low pressure and the desire to minimize high temperature residence times. The subject invention has a second advantage in that it produces a small amount of water vapor which will normally have a beneficial effect on the stability of the preferred dehydrogenation catalyst system. A third benefit of the subject process is the reduction in the hydrogen concentration present in downstream dehydrogenation stages, which tend to favor higher conversion rates.

The subject process may be employed with a wide range of feedstocks. The feed hydrocarbon may therefore include $C_6$-plus cyclic and acyclic hydrocarbons including $C_6$ paraffins, $C_7$ paraffins, ethylbenzene and other alkylaromatic hydrocarbons. However, it is preferred that the feedstock comprises a light hydrocarbon, a term used herein to refer to a hydrocarbon having less than 6 carbon atoms per molecule including ethane. The preferred feed material is a $C_3$-$C_5$ paraffin, with $C_3$-$C_4$ paraffins being highly preferred and with propane being especially preferred. The utilization of the subject process with any particular hydrocarbon will of course depend on an economic evaluation of the cost of utilizing the subject process versus the benefits which it provides.

The conditions which will be employed in the various reaction zones of the process will vary depending on such factors as catalyst activity, feedstock, and desired conversion. A general range of conditions which may be employed for dehydrogenation include a temperature of from about 550° C. to about 800° C., a pressure of from about 0.5 to about 20 atmospheres absolute and a liquid hourly space velocity between about 0.5 and 20 $hr^{-1}$. For the dehydrogenation of propane, the preferred conditions include a temperature in the range of about 600° C. to 700° C., a pressure from 1.0 to 3.0 atmospheres, a liquid hourly space velocity of about 1 to 8 $hr^{-1}$ and a hydrogen to total hydrocarbon ratio between 1.0:1.0 and 5.0:1.0. It is especially preferred that the inlet temperature to each bed of propane dehydrogenation catalyst is between 650° C. and 690° C. The pressure in all the reaction zones employed within the process preferably differs only by the incidental pressure drop which occurs as the reactants pass through the overall reaction system. The pressure maintained in the hydrogen oxidation zones is therefore essentially the same as the pressure in the corresponding immediately downstream dehydrogenation stage. The inlet temperature of each bed of oxidation catalyst is preferably between 10 and 20 Centigrade degrees below the desired inlet temperature of the immediately downstream bed of dehydrogenation catalyst. Larger temperature increases in the oxidation zones may be possible and desired depending on the selectivity of the oxidation catalyst and the tolerance of the dehydrogenation catalyst to water in the reactants.

The dehydrogenation zone preferably comprises at least one radial flow reactor in which the catalyst gradually moves downward by gravity flow to allow the rear continuous replacement of used catalyst with catalyst having a higher activity. Preferably, this replacement catalyst is regenerated in the appropriate facilities after being removed from the lowermost portion of the unitary multistage dehydrogenation reaction zone. It is preferred that a multistage reaction zone in which the reactants make at least two, preferably three, passes through a catalyst bed is employed. The dehydrogenation catalyst therefore preferably enters the top of a single unitary outer vessel containing the separate dehydrogenation stages and flows downward through the vessel from stage to stage by the action of gravity. A detailed description of moving bed reactors may be obtained by reference to U.S. Pat. Nos. 3,647,680; 3,652,231; 3,706,536; 3,785,963; 3,825,116; 3,839,196; 3,839,197; 3,854,887; and 3,856,662. It is also preferred that the beds of oxidation catalyst are located outside of the unitary vessel which houses the dehydrogenation stages.

The preferred propane dehydrogenation catalyst is comprised of a platinum group component, a tin component and an alkali metal component and a porous inorganic carrier material. Other catalytic compositions may be used within this zone if desired.

It is preferred that the porous carrier material of the dehydrogenation catalyst is an absorptive high surface area support having a surface area of about 25 to about 500 m$^2$/g. The porous carrier material should be relatively refractory to the conditions utilized in the reaction zone and may be chosen from those carrier materials which have traditionally been utilized in dual-function hydrocarbon conversion catalysts. A porous carrier material may therefore be chosen from an activated carbon, coke or charcoal, silica or silica gel, clays and silicates including those synthetically prepared and naturally occurring, which may or may not be acid-treated, as for example attapulgus clay, diatomaceous earth, kieselguhr, bauxite; refractory inorganic oxides such as alumina, titanium dioxide, zirconium dioxides, magnesia, silica-alumina, alumina-boria, etc.; crystalline aluminosilicates such as naturally occurring or synthetically prepared mordenite or a combination of one or more of these materials. The preferred porous carrier material is a refractory inorganic oxide, with the best results being obtained with an alumina carrier material. The crystalline aluminas, such as gamma-alumina, give the best results. In general the preferred catalyst will have a gamma-alumina carrier which is in the form of spherical particles having a relatively small diameter on the order of about 1/16-inch.

The preferred alumina carrier material for the dehydrogenation catalyst may be prepared in any suitable manner. For example, the alumina carrier may be prepared by adding a suitable alkaline reagent, such as ammonium hydroxide, to a salt of aluminum such as aluminum chloride in an amount to form an aluminum hydroxide gel which upon drying and calcining is converted to alumina. It is particularly preferred that alumina spheres are manufactured by the well-known oil drop method which comprises forming an alumina hydrosol by the techniques taught in the art, and preferably by reacting aluminum metal with hydrochloric acid, and combining the hydrosol with a suitable gelling agent. The resultant mixture is dropped into an oil bath maintained at elevated temperatures. The droplets remain in the oil bath until they set and form hydrogel spheres. The spheres are then continuously withdrawn from the oil bath and are normally subjected to specific aging treatments in oil and an ammoniacal solution to further improve their physical characteristics. The resulting pellets are then washed and dried at relatively low temperatures of about 150° C. to about 200° C. and calcined at a temperature of about 450° C. to about 700° C. for a period of about 1 to about 20 hours. See the teachings of U.S. Pat. Nos. 2,620,314 and 4,250,058 for additional details on the preparation of the base material by the oil drop method.

The preferred dehydrogenation catalyst also contains a platinum group component. Of the platinum group metals, which include palladium, rhodium, ruthenium, osmium and iridium, the use of platinum is preferred. The platinum group component may exist within the final catalyst composite as a compound such as an oxide, sulfide, halide, oxysulfide, etc., or as an elemental metal or in combination with one or more other ingredients of the catalyst. It is believed that best results are obtained when substantially all the platinum group component exists in the elemental state. The platinum group component generally comprises from about 0.01 to about 2 wt.% of the final catalytic composite, calculated on an elemental basis. It is preferred that the platinum content of the catalyst is between about 0.1 and 1.0 wt.%. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble, decomposable compound of a platinum group metal to impregnate the calcined carrier material. For example, the platinum group component may be added to the support by commingling the support with an aqueous solution of chloroplatinic or chloropalladic acid. An acid such as hydrogen chloride is generally added to the impregnation solution to aid in the distribution of the platinum group component throughout the carrier material.

The tin component of the preferred dehydrogenation catalyst should constitute about 0.01 to about 5 wt.% of the final composite, calculated on an elemental basis, although substantially higher amounts of tin may be utilized in some cases. Best results are often obtained with about 0.1 to about 1 wt.% tin. It is preferred that the atomic ratio of tin to platinum is between 1:1 and about 6:1. The tin component may be incorporated into the catalytic composite in any suitable manner known to effectively disperse this component in a very uniform manner throughout the carrier material. Thus, the component may be added to the carrier by coprecipitation. A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into the oil bath as previously described. The tin component may also be added through the utilization of a soluble, decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The preferred catalyst contains an alkali metal component chosen from cesium, rubidium, potassium, sodium, and lithium. The preferred alkali metal is normally either potassium or lithium depending on the feed hydrocarbon. The concentration of the alkali metal may range from between 0.1 and 3.5 wt.% but is preferably between 0.2 and about 2.5 wt.% calculated on an elemental basis. This component may be added to the catalyst by the methods described above as a separate step or simultaneously with the addition of another component. With some alkali metals, it is normally necessary to limit the halogen content to less than 0.5 wt.% and preferably less than 0.1 wt.%.

The oxidation catalyst employed in the subject process may be any commercially suitable catalyst which meets the required standards for stability and activity and which possesses high selectivity for the oxidation of hydrogen as compared to the oxidation of the feed or product hydrocarbon. That is, the oxidation catalyst must have a high selectivity for the oxidation of hydrogen with only small amounts of the feed or product hydrocarbon being oxidized. The preferred oxidation catalyst comprises a Group VIII noble metal and a metal or metal cation which possesses a crystal ionic radius greater than 1.3 A, with both of these materials being present in small amounts on a refractory solid support. The preferred Group VIII metals are platinum and palladium, but the use of ruthenium, rhodium, osmium and iridium is also contemplated. The Group VIII metal is preferably present in an amount equal to 0.01 to 5.0 wt.% of the finished catalyst. The metal or metal cation having a radius greater than 1.3 A is preferably chosen from Groups IA or IIA and is present in an amount equal to about 0.01 to about 10.0 wt.% of the finished catalyst. This component of the catalyst is preferably potassium or cesium, but the use of other metals including rubidium, strontium and barium is also contemplated.

The preferred solid support for the oxidation catalyst is alumina having a surface area between 1 and 300 m$^2$/g, an apparent bulk density of between about 0.2 and 1.5 g/cc, and an average pore size greater than 20 A. The metal-containing components are preferably impregnated into solid particles of the solid support by immersion in an aqueous solution followed by drying and calcination at a temperature of from about 500° C. to 600° C. in air. The support may be in the form of spheres, pellets or extrudates. The total amount of oxidatin catalyst used in the process is preferably less than 30 wt.% of the total amount of dehydrogenation catalyst and more preferably is between 5 and 15 wt.% of this total amount of dehydrogenation catalyst. The number of beds of oxidation catalyst and of dehydrogenation catalyst is preferably equal and may range between two and six, with the use of three beds of each catalyst being preferred. The beds of oxidation catalyst are preferably fixed, as compared to the preferred moving beds of hydrogenation catalyst, and the reactants preferably pass through a cylindrical bed of the oxidation catalyst.

The conditions utilized during the contacting of the reactant streams with the different beds of oxidation catalyst will be to a large extent set by the previously referred to dehydrogenation conditions. The preferred outlet temperature of any bed of oxidation catalyst is the preferred inlet of the immediately downstream bed of dehydrogenation catalyst. The temperature rise across any bed of oxidation catalyst is preferably less than 60 Centigrade degrees and more preferably less than 30 Centigrade degrees. The amount of oxidation catalyst which is used in each oxidation zone is much less than the amount of dehydrogenation catalyst employed in each dehydrogenation stage. Accordingly, the space velocities through the oxidation catalysts are higher, and may range between about 0.5 and 20 hr$^{-1}$. The liquid hourly space velocity, based on the liquid hydrocarbon charge at 60° F., is preferably between 2 and 10 hr$^{-1}$. It is preferred that substantially all of the oxygen which enters a bed of oxidation catalyst is consumed within that bed of oxidation catalyst and that the effluent stream of any bed of oxidation catalyst contains less than 0.1 mole percent oxygen. The total amount of oxygen charged to the process is preferably regulated such that the dehydrogenation zone effluent stream contains less than about 2.0 mole percent water and more preferably less than 1.5 mole percent water. This preference is entirely related to the characteristics of the preferred dehydrogenation catalyst, and greater oxygen addition rates resulting in water contents of 10 percent or more may be employed if desired. A different amount of oxygen may be passed into each bed of oxidation catalyst but it is preferred that no individual bed receives more than 150 vol.% of the amount charged to any other bed. The oxygen source may be air, but it is preferred that an oxygen-enriched gas containing less than 5 mole percent of nitrogen or other impurities is used as the oxygen source. To avoid any cooling of the heater effluent the oxygen containing gas stream should be heated to a temperature equal to or greater than the temperature of the heater effluent stream as by small electric heaters.

One embodiment of the subject process may be characterized as a process for the dehydrogenation of C$_3$-C$_5$ paraffins which comprises the steps of admixing oxygen into a heated feed stream comprising a C$_2$-C$_5$ paraffin and hydrogen and which has a temperature above 600° C.; heating the feed stream by at least 10 Centigrade degrees by contacting the feed stream with a firsst bed of oxidation catalyst which selectively promotes the reaction of hydrogen and oxygen and thereby forming a first oxidation zone effluent stream; contacting the first oxidation zone effluent stream with a first bed of dehydrogenation catalyst maintained at dehydrogenation conditions and located within the dehydrogenation zone, and thereby forming a first dehydrogenation stage effluent stream; heating the first dehydrogenation stage effluent stream by indirect heat exchange; admixing oxygen into the first dehydrogenation stage effluent stream, and heating the first dehydrogenation stage effluent by contact with a second bed of oxidation catalyst which selectively promotes the reaction of hydrogen and oxygen and thereby forming a second oxidation zone effluent stream; contacting the second oxidation zone effluent stream with a second bed of dehydrogenation catalyst maintained at dehydrogenation conditions and located within the dehydrogenation zone, and thereby forming a second dehydrogenation stage effluent stream; removing a dehydrogenation zone effluent stream comprising hydrogen, a product C$_2$-C$_5$ acyclic olefin and the feed C$_2$-C$_5$ paraffin from the dehydrogenation zone; and recovering the C$_2$-C$_5$ acyclic olefin from the dehydrogenation zone effluent stream.

A consideration in the overall design of the equipment used in performing the subject process is the residence time of the reactants in the transfer lines connecting the outlet of the heater to the inlet of the dehydrogenation zone. This time will normally be held to a minimum. However, the customary size and design of fixed process heaters and the design of the preferred stacked moving bed reaction zone combine to require rather lengthy transfer lines between these two points. One positive step in the subject process is the tranportation or movement of the heated reactants from the outlet of the heater to a point close to the inlet of the next bed of dehydrogenation catalyst prior to the oxidative heating of the reactants. Rather than attempt to define the relative proximity which is sufficient to achieve this step it is more convenient to refer to the residence time of the reactants between various points in the process. Residence time rather than actual physical location is also the best measure of the exposure of the feed hydrocarbon to the undesired high temperature conditions. The residence time which it is desired to reduce is that during which the feed hydrocarbon has its maximum temperature, which is the time between leaving a bed of oxidation catalyst and entering the immediately downstream bed of dehydrogenation catalyst. For instance, the length of time between when the effluent of the second bed of oxidation catalyst leaves the second bed of oxidation catalyst and enters the second bed of dehydrogenation catalyst should be less than 40 percent of the length of time between when the effluent of the first bed of dehydrogenation catalyst has been heated by indirect heat exchange and the effluent of the second bed of oxidation catalyst enters the second bed of dehydrogenation catalyst. Preferably, this percentage is less than 25 and more preferably less than 10. A similar preference exists for the residence time of the reactants between each dehydrogenation stage and the bed of oxidation catalyst located upstream of it.

The product dehydrogenated hydrocarbons may be recovered in a conventional product recovery system such as previously described or as presented in the cited references. In the particular case of propane and butane it is preferred that the effluent of the dehydrogenation zone is first cooled by heat exchange against the feed stream and then subjected to further cooling using air or cooling water as a coolant. The effluent stream is then compressed, again cooled, dried, and further cooled by heat exchange against a cold recycle hydrogen stream. The effluent stream is passed into a vapor-liquid separation zone with the liquid phase produced in this manner being passed into a light ends stripping column. A mixture of the feed and product hydrocarbons is removed from the stripping column as a bottoms product stream. The hydrogen-rich vapor phase removed from the separation zone is cooled by expansion in a power recovery turbine and thereby converted to the cold recycle hydrogen stream.

I claim as my invention:

1. A process for the dehydrogenation of hydrocarbons which comprises the steps of:
   (a) admixing oxygen into a heated feed stream comprising a $C_2$–$C_8$ hydrocarbon and hydrogen;
   (b) heating the feed stream by contacting the same with a first bed of oxidation catalyst which preferentially oxidizes hydrogen as compared to the $C_2$–$C_8$ hydrocarbon;
   (c) contacting the effluent of the first bed of oxidation catalyst with a first bed of dehydrogenation catalyst located within a dehydrogenation zone;
   (d) heating the effluent of the first bed of dehydrogenation catalyst by indirect heat exchange;
   (e) admixing oxygen into the heated effluent of the first bed of dehydrogenation catalyst;
   (f) contacting the effluent of the first bed of dehydrogenation catalyst with a second bed of oxidation catalyst;
   (g) contacting the effluent of the second bed of oxidation catalyst with a second bed of dehydrogenation catalyst located within the dehydrogenation zone;
   (h) recovering a dehydrogenated hydrocarbon corresponding to the $C_2$–$C_8$ hydrocarbon from a dehydrogenation zone effluent stream which is withdrawn from the dehydrogenation zone; and,
   (i) recovering hydrogen from the dehydrogenation zone effluent stream and recycling at least a portion of the hydrogen to the dehydrogenation zone as part of said feed stream.

2. The process of claim 1 further characterized in that the feed stream comprises a $C_2$–$C_5$ paraffin.

3. The process of claim 2 further characterized in that the paraffin is propane.

4. The process of claim 3 further characterized in that the heated effluent of the first bed of dehydrogenation catalyst has a temperature below 650° C. prior to entering the second bed of oxidation catalyst.

5. The process of claim 4 further characterized in that the effluent stream of the second bed of oxidation catalyst has a temperature above 655° C.

6. The process of claim 1 further characterized in that the length of time between when the effluent of the second bed of oxidation catalyst leaves the second bed of oxidation catalyst and the effluent of the second bed of oxidation catalyst enters the second bed of dehydrogenation catalyst is less than 40 percent of the length of time between when the effluent of the first bed of dehydrogenation catalyst has been heated and the effluent of the second bed of oxidation catalyst enters the second bed of dehydrogenation catalyst.

7. The process of claim 6 further characterized in that the first and the second beds of dehydrogenation catalyst are located within a single unitary vessel and the second bed of oxidation catalyst is located outside of said unitary vessel.

8. The process of claim 1 further characterized in that the oxygen which is admixed into the feed stream and into the effluent of the first bed of dehydrogenation catalyst is derived from an oxygen supply stream which comprises less than 5 mole percent nitrogen.

9. The process of claim 1 further characterized in that the first and the second beds of dehydrogenation catalyst and the second bed of oxidation catalyst are located within a single unitary vessel.

10. The process of claim 1 further characterized in that three beds of dehydrogenation catalyst are utilized in the process.

11. A process for the dehydrogenation of $C_2$–$C_5$ paraffins which comprises the steps of:
    (a) admixing oxygen into a heated feed stream comprising a $C_2$–$C_5$ paraffin and hydrogen and which has a temperature above 600° C.;
    (b) heating the feed stream by at least 10 Centigrade degrees by contacting the feed stream with a first bed of oxidation catalyst which selectively promotes the reaction of hydrogen and oxygen and thereby forming a first oxidation zone effluent stream;
    (c) contacting the first oxidation zone effluent stream with a first bed of dehydrogenation catalyst maintained at dehydrogenation conditions and located within a dehydrogenation zone, and thereby forming a first dehydrogenation stage effluent stream;
    (d) heatng the first dehydrogenation stage effluent stream by indirect heat exchange;
    (e) admixing oxygen into the first dehydrogenation stage effluent stream, and heating the first dehydrogenation stage effluent by contact with a second bed of oxidation catalyst which promotes the reaction of hydrogen and oxygen and thereby forming a second oxidation zone effluent stream;
    (f) contacting the second oxidation zone effluent stream with a second bed of dehydrogenation catalyst maintained at dehydrogenation conditions and located within the dehydrogenation zone, and thereby forming a second dehydrogenation stage effluent stream;
    (g) removing a dehydrogenation zone effluent stream comprising hydrogen, a $C_2$–$C_5$ acyclic olefin and the $C_2$–$C_5$ paraffin from the dehydrogenation zone; and, (h) recovering the $C_2$-$C_5$ acyclic olefin from the dehydrogenation zone effluent stream.

12. The process of claim 11 further characterized in that the feed stream comprises butane.

13. The process of claim 11 further characterized in that the feed stream comprises propane.

14. The process of claim 13 further characterized in that the feed stream enters the first bed of oxidation catalyst at a temperature below about 650° C.

15. The process of claim 11 further characterized in that the dehydrogenation zone comprises three separate beds of dehydrogenation catalyst.

16. The process of claim 11 further characterized in that the first dehydrogenation stage effluent stream is not heated to a temperature above about 650° C. by indirect heat exchange.

17. The process of claim 16 further characterized in that at least three dehydrogenation stages located within a single unitary outer vessel are employed in the process.

18. The process of claim 17 further characterized in that the beds of oxidation catalyst employed in the process are located outside of the outer vessel containing the dehydrogenation stages.

19. The process of claim 17 further characterized in that the dehydrogenation catalyst gradually moves downward through said unitary outer vessel by the action of gravity and travels through different dehydrogenation stages.

20. The process of claim 11 further characterized in that the length of time between when the second oxidation stage effluent stream leaves the second bed of oxidation catalyst and contacts the second bed of dehydrogenation catalyst is less than 25 percent of the time between when the first dehydrogenation stage effluent stream was heated by indirect heat exchange and the second oxidation stage effluent stream contacts the second bed of dehydrogenation catalyst.

* * * * *